US011229347B2

(12) United States Patent
Katballe et al.

(10) Patent No.: US 11,229,347 B2
(45) Date of Patent: Jan. 25, 2022

(54) ENDOSCOPY SYSTEM

(71) Applicant: SURGERYTECH APS, Aarhus N (DK)

(72) Inventors: Niels Katballe, Lystrup (DK); Peter Heydorn Kristensen, Knebel (DK)

(73) Assignee: SURGERYTECH APS, Aarhus N (DK)

(*) Notice: Subject to any disclaimer, the term of this patent is extended or adjusted under 35 U.S.C. 154(b) by 117 days.

(21) Appl. No.: 16/416,953

(22) Filed: May 20, 2019

(65) Prior Publication Data
US 2019/0282072 A1 Sep. 19, 2019

Related U.S. Application Data

(63) Continuation of application No. PCT/EP2018/083383, filed on Dec. 3, 2018.

(30) Foreign Application Priority Data

Dec. 8, 2017 (GB) .................................. 1720531.1

(51) Int. Cl.
A61B 1/00 (2006.01)
A61B 1/018 (2006.01)
(Continued)

(52) U.S. Cl.
CPC ...... A61B 1/00154 (2013.01); A61B 1/00066 (2013.01); A61B 1/00071 (2013.01);
(Continued)

(58) Field of Classification Search
CPC . A61B 1/00154; A61B 1/018; A61B 1/00071; A61B 1/00066; A61B 1/273;
(Continued)

(56) References Cited

U.S. PATENT DOCUMENTS 5,261,416 A  11/1993 Taussig
5,509,909 A   4/1996 Moy
(Continued)

FOREIGN PATENT DOCUMENTS

CN  104510436      4/2015
EP  2 959 823 A1  12/2015
(Continued)

OTHER PUBLICATIONS

International Search Report and Written Opinion for corresponding Patent Application No. PCT/EP2011/002325, dated Aug. 11, 2011, 17 pages.

Primary Examiner — Timothy J Neal
Assistant Examiner — Genja M Frankert
(74) Attorney, Agent, or Firm — Crowell & Moring LLP

(57) ABSTRACT

According to the present invention, there is provided an endoscopy system comprising an endoscope guide and an endoscope. The endoscope of the system comprises a proximal end and a distal end. The endoscope guide of the system comprises a proximal end, a mid-section comprising at least one endoscope entry port, a distal end comprising at least one endoscope exit port, a lumen capable of receiving an endoscope extending from the at least one entry port to the at least one exit port and at least one bend located between the at least one entry port and the at least one exit port. The endoscope guide is capable of directing the insertion of the distal end of the endoscope into a body cavity when the distal end of the endoscope exits the endoscope exit port and the distal end of the endoscope guide is also configured so as to be capable to be retained within the body cavity during a surgical procedure so as to control the positioning of the distal end of the endoscope within the body cavity.

18 Claims, 12 Drawing Sheets

(51) Int. Cl.
 A61B 1/012 (2006.01)
 A61B 1/01 (2006.01)
 A61B 1/267 (2006.01)
 A61B 1/273 (2006.01)
(52) U.S. Cl.
 CPC ...... *A61B 1/00135* (2013.01); *A61B 1/00142* (2013.01); *A61B 1/01* (2013.01); *A61B 1/018* (2013.01); *A61B 1/0125* (2013.01); *A61B 1/267* (2013.01); *A61B 1/273* (2013.01)
(58) Field of Classification Search
 CPC ... A61B 1/267; A61B 1/00142; A61B 1/0125; A61B 1/01; A61B 1/00135; A61B 17/3421; A61B 1/0052; A61B 2017/3445; A61B 90/50; A61B 2017/00331; A61B 5/0084; A61B 2034/301; A61B 1/313; A61M 25/10186; A61M 25/0662; A61M 25/0026; A61M 16/0418; A61M 16/04; A61M 25/01
 See application file for complete search history.

(56) References Cited

U.S. PATENT DOCUMENTS

| | | | |
|---|---|---|---|
| 5,536,255 | A | 7/1996 | Moss |
| 5,620,408 | A * | 4/1997 | Vennes .............. A61B 1/00154 128/200.26 |
| 6,270,476 | B1 | 8/2001 | Santoianni et al. |
| 6,585,639 | B1 * | 7/2003 | Kotmel .............. A61B 1/00082 600/114 |
| 6,592,575 | B1 | 7/2003 | Kesten et al. |
| 2002/0032432 | A1 | 3/2002 | Nash et al. |
| 2002/0052576 | A1 | 5/2002 | Massengale |
| 2005/0038406 | A1 | 2/2005 | Epstein et al. |
| 2005/0107664 | A1 | 5/2005 | Kalloo et al. |
| 2005/0143690 | A1 | 6/2005 | High |
| 2006/0009801 | A1 | 1/2006 | McGurk et al. |
| 2006/0063973 | A1 * | 3/2006 | Makower ........... A61B 1/00135 600/114 |
| 2006/0184188 | A1 * | 8/2006 | Li ..................... A61B 17/1617 606/180 |
| 2007/0167682 | A1 * | 7/2007 | Goldfarb ........... A61B 1/00154 600/114 |
| 2007/0293727 | A1 * | 12/2007 | Goldfarb ........... A61B 1/00135 600/178 |
| 2008/0015625 | A1 * | 1/2008 | Ventura ............. A61B 17/3439 606/191 |
| 2008/0188868 | A1 * | 8/2008 | Weitzner ........... A61B 1/00154 606/130 |
| 2008/0249356 | A1 | 10/2008 | Motai et al. |
| 2008/0319266 | A1 * | 12/2008 | Poll .................... A61B 1/00094 600/157 |
| 2009/0281376 | A1 * | 11/2009 | Acosta ............... A61B 17/3421 600/104 |
| 2009/0287045 | A1 * | 11/2009 | Mitelberg .......... A61B 1/00082 600/104 |
| 2009/0306471 | A1 * | 12/2009 | Gettman ........... A61M 25/0662 600/104 |
| 2010/0063360 | A1 * | 3/2010 | Harrington ........ A61B 17/3415 600/159 |
| 2010/0130821 | A1 * | 5/2010 | Rosemurgy ........ A61B 1/00137 600/115 |
| 2010/0241155 | A1 * | 9/2010 | Chang ............... A61M 25/0068 606/196 |
| 2011/0082456 | A1 * | 4/2011 | Welt .................... A61B 17/295 606/45 |
| 2011/0092963 | A1 * | 4/2011 | Castro ............... A61B 17/3421 606/1 |
| 2012/0018011 | A1 * | 1/2012 | Koga ................. A61B 1/00119 137/511 |
| 2012/0197084 | A1 * | 8/2012 | Drach ............... A61B 17/3474 600/123 |
| 2014/0005480 | A1 * | 1/2014 | Wagner .................. A61B 1/018 600/123 |
| 2014/0088371 | A1 * | 3/2014 | Vayser .............. A61B 1/00135 600/249 |
| 2016/0367119 | A1 * | 12/2016 | Ouyang ............. A61B 1/00034 |
| 2017/0055811 | A1 * | 3/2017 | Germain ............ A61B 1/00135 |
| 2017/0340191 | A1 * | 11/2017 | Zeng ................. A61B 1/00154 |
| 2018/0008126 | A1 * | 1/2018 | Arai .................. A61B 1/00154 |
| 2018/0092635 | A1 * | 4/2018 | Csiky ..................... A61B 90/50 |
| 2018/0140176 | A1 * | 5/2018 | Sinha .................... A61B 1/008 |
| 2018/0192855 | A1 * | 7/2018 | Sakai ..................... A61B 1/0055 |
| 2019/0014980 | A1 * | 1/2019 | Herskovic .......... A61B 1/00052 |
| 2019/0217034 | A1 * | 7/2019 | Maslow .................. A61B 1/01 |

FOREIGN PATENT DOCUMENTS

| | | |
|---|---|---|
| JP | 08052220 | 2/1996 |
| WO | WO1997/010749 | 3/1997 |
| WO | 2009/029655 A1 | 5/2009 |
| WO | WO2009/098445 A1 | 8/2009 |
| WO | WO2011/141162 A2 | 11/2011 |
| WO | 2018/003925 A1 | 4/2018 |
| WO | 2018/008433 A1 | 11/2018 |

* cited by examiner

ENDOSCOPY SYSTEM

The present invention is directed towards an endoscopy system comprising an endoscope guide and an endoscope for use in a surgical procedure. The surgical procedure involves introducing and manoeuvring the endoscope of the system in a body cavity of an individual using the endoscope guide.

An endoscope is an optionally illuminated optical, typically slender and tubular, instrument used to look into the body and used in procedures called endoscopy.

Endoscopes can be inserted into the body through a natural opening to a body cavity, such as through the mouth and down the throat. An endoscope can also be inserted through a small cut (incision) made in the skin, thus forming an entry to a body cavity, when keyhole surgery is being carried out. The endoscope may be inserted into such an incision or through a natural opening directly, or the endoscope may be introduced through a straight and rigid guide.

Once in the body cavity, the positioning of the endoscope may be manipulated by moving the endoscope itself, or moving the straight rigid guide, and/or incorporating a bendable tip on the endoscope. Therefore, the range of movement and function of endoscopes currently used is limited.

The present invention provides a system comprising an endoscope guide and endoscope which overcomes drawbacks of currently used systems and allows a much greater field of movement and orientation of the endoscope within a body cavity. Thus, the present invention allows for greater control of a surgical procedure.

According to the present invention, there is provided an endoscopy system comprising an endoscope guide and an endoscope, wherein the endoscope comprises:
- a proximal end; and
- a distal end;

wherein, the endoscope guide comprises:
- a proximal end;
- a mid-section comprising at least one endoscope entry port;
- a distal end comprising at least one endoscope exit port;
- a lumen capable of receiving an endoscope extending from the at least one entry port to the at least one exit port; and
- at least one bend located between the at least one entry port and the at least one exit port;
- wherein, the endoscope guide is capable of directing the insertion of the distal end of the endoscope into a body cavity when the distal end of the endoscope exits the endoscope exit port and the distal end of the endoscope guide is also configured so as to be capable to be retained within the body cavity during a surgical procedure so as to control the positioning of the distal end of the endoscope within the body cavity.

Preferably, the endoscope is a laryngoscope, esophagoscope, thoracoscope, pleuroscope, laparoscope, bronchoscope, mediastinoscope, gastroscope or an amnioscope, preferably wherein the endoscope is a thoracoscope or a laparoscope.

Advantageously, the endoscope guide comprises a gas insufflation connector.

Conveniently, the endoscope guide comprises a one-way valve located in the lumen between the at least one entry port and the at least one exit port, wherein the valve is configured so as to prevent gas from passing out of the body cavity through the lumen of the endoscope guide.

Advantageously, there is a functional relationship between the movement of the proximal end of the endoscope guide and the distal end of the endoscope guide, so that the orientation of the proximal end of the endoscope guide defines the orientation in which the distal end of the endoscope located in the lumen of the endoscope guide exits the exit port of the endoscope guide in the body cavity.

Preferably, the mid-section is an essentially straight section.

Conveniently, the endoscope guide comprises at least one bend located between the mid-section and the proximal end.

Advantageously, the proximal end of the endoscope guide comprises a handle.

Preferably, the proximal section of the endoscope guide defines a proximal axis, the distal section of the endoscope guide defines a distal axis and the proximal axis and distal axis are essentially parallel to one another so that the direction of exit of the endoscope from the at least one exit port is essentially the same as the direction of the proximal axis of the proximal section. Alternatively, the angle between the proximal section and the mid-section may be adjustable to provide optimal ergonomic conditions during the procedure.

Conveniently, the body cavity is a thoracic cavity, an abdominal cavity or a pelvic cavity of an animal or human body.

Advantageously, the endoscope guide comprises a collar with a diameter larger than the diameter of the endoscope guide, preferably wherein the collar is located between the at least one entry port and the distal bend.

According to another aspect of the invention, there is provided a method for inserting an endoscope into a body cavity of an individual comprising the steps of providing an endoscopy system according to any preceding claim and inserting the endoscope into the body cavity of the individual using the endoscope guide.

According to a further aspect of the invention, there is provided a kit-of-parts comprising an endoscopy system according to the invention in the form of a sterile, pre-packaged kit-of-parts for single use.

Definitions

Proximal end: defines the end of the endoscope and endoscope guide closer and accessible to the medical practitioner when these are in use. In other words, it is the end of the endoscope and the endoscope guide which is farther away from the desired position of the body cavity, when in use.

Distal end: defines the end of the endoscope and endoscope guide farther away from the medical practitioner when these are in use. In other words, it is the end of the endoscope and the endoscope guide which is closer to the desired position of the body cavity, when the guide is in use, and, in the endoscope guide, this includes the endoscope exit port.

Proximal section: the proximal section defines a part of the endoscope and the endoscope guide which is accessible to the medical practitioner when in use. In other words, it is the section of the endoscope or endoscope guide which is farther away from the desired position in the body when in use. Typically, the proximal section, therefore, includes the proximal end. In another embodiment of the invention, the endoscope guide may not include the proximal section and, in this case, a part of a mid-section may be considered as the proximal section.

Distal section: defines a part of the endoscope and the endoscope guide which is farther away from the medical practitioner when in use. In other words, it is the section of the endoscope or endoscope guide which is closer to the desired position in the body, when in use. The distal section includes the distal end, which, in the endoscope guide, includes the endoscope exit port.

Mid-section: The mid-section defines a part of the endoscope guide connecting the proximal section and the distal section. In some circumstances, the mid-section includes the proximal end. The person skilled in the art would appreciate that in such situations, a small part of the mid-section including and near the proximal end may be considered as a proximal section for understanding purposes and therefore, complies with the requirement that the proximal end is closer and accessible to the medical practitioner when the endoscope guide is in use. The mid-section includes the entry port for allowing the endoscope to be introduced in the endoscope guide.

Proximal axis: Axis along the length of the proximal section of the endoscope guide and forms a proximal angle with a mid-axis of the mid-section.

Distal axis: Axis along the length of the distal section of the endoscope guide and forms a distal angle with a mid-axis of the mid-section. In one embodiment, the direction of the distal axis may be in the same direction to that of the proximal axis. The person skilled in the art would appreciate that the directions of the proximal axis and the distal axis are not limited to the previous embodiment because the proximal axis and the distal axis may form other angles between each other as well.

Mid-axis: Axis along the length of the mid-section of the endoscope guide and forms a proximal angle with the proximal axis and a distal angle with the distal axis respectively.

Proximal angle: Angle formed between the proximal axis and mid-axis of the endoscope guide at a proximal bend.

Distal angle: Angle formed between the distal axis and mid-axis of the endoscope guide at a distal bend.

Proximal bend: Bend formed in the endoscope guide between the proximal section (defined by proximal axis) and the mid-section (defined by the mid-axis) because of the proximal angle.

Distal bend: Bend formed in the endoscope guide between the distal section (defined by distal axis) and the mid-section of the endoscope guide (defined by the mid-axis) because of the distal angle.

BRIEF DESCRIPTION OF THE DRAWINGS

The embodiments of the invention, together with its advantages, may be best understood from the following detailed description taken in conjunction with the accompanying figures where same features are represented by the same numerals.

DETAILED DESCRIPTION OF THE INVENTION

Figure 1:
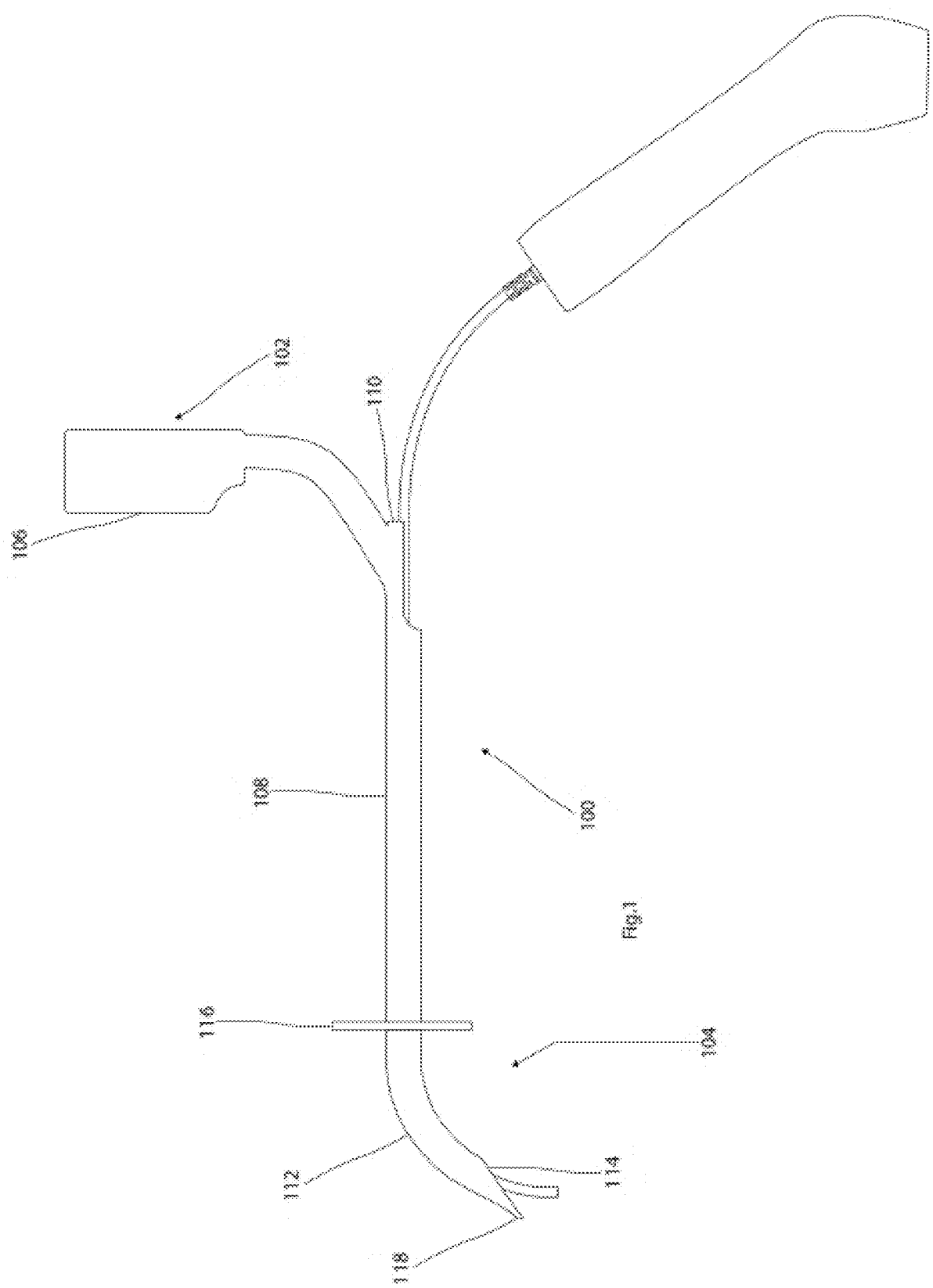
FIG. 1 illustrates an embodiment of the endoscope guide of the system.

According to the invention, an endoscopy system comprising an endoscope guide and an endoscope is disclosed. The endoscope of the system comprises a proximal section, with a proximal end, and a distal section, with a distal end. The endoscope guide comprises a proximal section, with a proximal end, a mid-section, comprising at least one endoscope entry port and a distal section, and a distal end comprising at least one endoscope exit port. The endoscope guide also comprises a lumen capable of receiving an endoscope extending from the at least one entry port to the at least one exit port and at least one distal bend located between the at least one entry port and the at least one exit port. The endoscope guide of the invention is capable of directing the insertion of the distal end of the endoscope into a body cavity when the distal end of the endoscope exits the endoscope exit port and the endoscope guide is also configured so as to be capable to remain within the body cavity during a surgical procedure so as to control the positioning of the distal end of the endoscope within the body cavity.

The endoscope guide comprises a lumen into which an endoscope can be inserted through an entry port located in the mid-section. An endoscope exit port is located at the distal end of the endoscope guide. The entry port and the exit port are separated from each other by a distal bend or curved section. The exact form of the bent or curved section of the endoscope guide is not essential as long as the endoscope can be advanced through the lumen of the endoscope guide with relative ease under practical circumstances.

It is important for the functionality of the endoscope guide for at least one curved section to be located in the distal end of the device, which is located in a body cavity during use of the endoscope guide, so that a movement, including a rotation, of the proximal end of the endoscope guide, which is located outside the patient to be treated, by a medical practitioner during a method of surgery, will result in the positioning of the exit port of the endoscope guide in a position which defines an intended axial exit direction of the endoscope once the endoscope exits the exit port of the endoscope guide. The ability of being able to define an intended, axial exit direction of the endoscope is a requirement for the medical practitioner to be able to direct the endoscope accurately into and within a body cavity, in order to accurately locate the endoscope therein at an intended location.

A device not having a substantially curved section located in the distal end thereof, i.e. the end of the device which is located in a body cavity during use of the endoscope guiding device, does not allow the medical practitioner, under practical circumstances, to define in all cases an intended axial exit direction of the endoscope which enables the medical practitioner to accurately position and manoeuvre the endoscope in a body cavity of a patient during a method of surgery. The reason being that an essentially straight exit port section of the endoscope guide will restrict and limit the angle at which the exit port can be positioned in a body cavity once the endoscope guide is entered into the body cavity during a surgical method. The rotation of an endoscope guide having an essentially straight exit port section does not allow a medical practitioner to point the exit port of the device in all desirable directions once the endoscope guide has been entered into a body cavity during a surgical procedure.

Accordingly, it is the curved section of the distal end of the endoscope guide which ensures that when a medical practitioner operates, i.e. moves and/or rotates, the endoscope guide during use thereof and positions the distal opening of the guide in an intended position defining an intended, axial exit direction of the endoscope that an endoscope can exit the distal end of the endoscope guide located in a body cavity in a direction which is intended and required for being able to accurately position the endoscope at an intended position of a body cavity.

The at least one curved section of the endoscope guide located in the distal end of the endoscope guide can be operably connected to other parts of the endoscope guide. In one embodiment, the at least one curved section of the endoscope guide located in the distal end of the device operably connects the first and second openings of the guide, optionally in combination with other guide sections having other shapes and forms as required for the design of the endoscope guide, including guide sections having curved sections, such as arc formed shapes, as well as guide sections being at least essentially straight, i.e. non-angular in shape.

The endoscope exit port located in the extreme distal end of the endoscope guide can have a tapering end so as to facilitate entry of the endoscope into an incision of the skin of a patient's body, or other opening, while preferably retaining a uniform, internal diameter of the lumen of the endoscope guide. Alternatively, the exit port may be provided with a projecting tip. This tip may be in the form of a lip projecting beyond the exit port. Such a lip can aid the insertion of the guide into a patient's body.

The endoscope guide can comprise a collar with a diameter significantly larger than the diameter of the tube of the guiding device. The function of the collar is to prevent the endoscope guide from being entered too far into the body cavity of an individual under practical circumstances. The position of the collar on the endoscope guide will typically be somewhere between the distal bend or curved section and the mid-section of the endoscope guide. The collar should not limit the movement of the extreme distal end of the endoscope guide, but merely ensure that the distal end of the endoscope guide remains at a fixed depth within the body cavity without the risk of being inserted too far into the body cavity.

Endoscopes for inclusion in the system of the invention typically comprise a flexible tube and a light delivery system to illuminate the organ or object under inspection within a body cavity of a patient, wherein the light source is normally outside of the patient's body and the light is delivered to the body cavity via an optical fibre system. Endoscopes may also comprise other features such as cameras and additional channels (access channels) to allow entry of medical instruments or manipulators.

The endoscope may also comprise means to allow introduction of a gas, via an insufflation technique, into the body cavity of a patient in order to inflate the cavity allowing greater room for the distal end of the endoscope to be manoeuvred within the body cavity. The gas may be introduced through an access channel within the endoscope. The gas may be air, although it is preferable to use an inert gas such as carbon dioxide, nitrogen or noble gases, or mixtures of any of these gases. Preferably, carbon dioxide is used to inflate the body cavity.

In another embodiment, the gas may be introduced into the body cavity using the endoscope guide. In such embodiments, the gas may be introduced via a gas insufflation portion through the lumen extending from the at least one endoscope entry port to the at least one endoscope exit port. Alternatively, the endoscope guide may comprise a second lumen for introducing the gas. In either of these scenarios, the endoscope guide may comprise a gas insufflation connector for connecting to a gas source.

The gas insufflation portion allows for gas to be introduced through the guide and into the patient in order to facilitate use of the endoscope within the patient's body.

The gas insufflation portion may comprise a chamber formed by a section of the guide with a diameter which is larger than the diameter of the lumen of the guide, through which the endoscope may be passed. A gas inlet may be included which lead into the chamber and allows for the introduction of gas into the lumen of the guide, and thus into the patient's body.

The larger diameter of the chamber in relation to the diameter of the lumen of the guide is beneficial in that it provides a volume between the endoscope when placed within the lumen and the gas inlet. Without the volume, on being introduced into the lumen the space into which the gas is introduced immediately is restricted due to the presence of the endoscope in use, which leads to increase pressure within the lumen and increased gas flow. The presence of the chamber with larger diameter and, therefore, larger volume, allows for more precise control of the flow of gas into the lumen of the guide as the increase in pressure is much reduced.

Where the endoscope guide comprises a second lumen for gas insufflation, ideally the second lumen extends from the gas insufflation connector to the at least one exit port of the endoscope guide.

In an embodiment, the endoscope guide of the system comprises a valve located in the lumen between the at least one entry port and the at least one exit port. This valve is configured so as to prevent gas from passing out of the body cavity through the lumen of the endoscope guide.

Ideally, the valve is located within the endoscope guide proximally to the gas insufflation connector, which ensures that, on the distal end of the guide entering the body cavity, gas does not exit the body cavity through the lumen of the endoscope guide. The valve is preferably configured so as to allow the introduction of media (such as gas) or other instruments, particularly the endoscope, to pass through the lumen and valve of the endoscope guide with little hindrance. When the endoscope is passed through the lumen of the endoscope guide, it is preferable for the valve to form a substantially gas-tight seal around the endoscope so as to prevent gas in the body cavity from leaking through the lumen of the endoscope guide.

The endoscope guide may indeed include multiple valves, such as one, two or three valves, to provide an improved seal around the endoscope. Preferably, the endoscope guide comprises two valves.

In an embodiment, the valve or valves are located within the chamber of the gas insufflation portion and are positioned before the gas inlet, i.e. between the entry port and the gas inlet.

Preferably, the valve is a pinch valve, such as a duckbill type valve, which may be made out of rubber or a synthetic elastomer. One end of such a valve is fixedly attached to the inside of the lumen of the endoscope guide and the other end of the valve comprises an opening, where the opening is configured to naturally gradually taper to a flattened end where the opening of the valve is effectively sealed. Preferably, the valve is configured so as to taper in a direction away from the endoscope entry port and towards the endoscope exit port. When the distal end of the endoscope guide is located in a body cavity which is inflated with a gas, and therefore under pressure, the valve prevents backflow of the gas in the body cavity through the lumen of the endoscope guide as the tapered flattened ends of the valve remain sealed. However, the endoscope of the system may still pass through the valve from the direction of the endoscope entry port end of the guide and, in doing so, the flattened ends of the valve open up to allow the endoscope to pass, but form a seal around the circumference of the endoscope. Thus, retaining a substantially gas-tight seal around the endoscope. On retracting the endoscope, the valve returns to its natural tapered position thus sealing the valve once more.

Ideally, the gas insufflation connector is located between the valve and the at least one exit port of the endoscope guide. Although in embodiments where the guide comprises a gas insufflation connector without a valve, the gas insufflation connector is ideally located between the at least one entry port and the at least one exit port. More preferably, the gas insufflation connector is located between the at least one entry port and the distal bend of the guiding device.

Particularly suitable endoscopes for inclusion in the system include laryngoscopes, esophagoscopes, thoracoscopes, pleuroscopes, laparoscopes, bronchoscopes, mediastinoscopes, gastroscopes or amnioscopes, preferably the endoscope included in the system is a thoracoscope, pleuroscope or a laparoscope.

Preferably, the endoscope of the system comprises a bending section at the distal end, which may include a camera and a light delivery system. Such endoscopes allow the user to control the angle of the tip of the endoscope so as to alter the direction of view of the camera. The bending section may be controlled by a control lever located at the proximal end of the endoscope.

Typically, the bending section of such endoscopes can bend in two directions, up and down. Preferably, the bending section bends to an angle of from 90° to 150° in either direction, such as from 110° to 150°, more specifically from 130° to 150°. Ideally, the bending section of the endoscope bends up to an angle of 150° in either direction.

It is preferable for there to be a functional relationship between the movement of the proximal end of the endoscope guide and the distal end of the endoscope. The functional relationship may be determined by the measure of the distal angle of the distal bend and the length of the distal section. A person skilled in the art would appreciate that prior knowledge of the measure of the distal angle, and the length of the distal section, would allow the medical practitioner to operate or move the distal end of the endoscope guide in a controlled and reliable manner, in order to manoeuvre the distal end of the endoscope guide within the body cavity.

The functional relationship determines the position of the distal end of the endoscope guide in the body cavity; and defines the direction in which the endoscope exits the at least one exit port, the direction being along a distal axis.

A medical practitioner can divert the distal end of the endoscope guide through an incision defining an access port to a body cavity of a patient thereby locating the distal end of the endoscope guide in the body cavity. By moving the outer part of the endoscope guide (i.e. the part of the guide not inserted in the body cavity through the incision defining an access to the body cavity) side ways, or up or down, while also retaining the option of being able to rotate the guide along the axis defined by the incision, the medical practitioner has essentially full freedom to adjust and decide the axial direction in which the endoscope is to exit the exit port of the guide and enter the body cavity, during insertion therein, prior to being accurately positioned at an intended position of the body cavity defined by direction and distance relative to the point of entry of the pleural cavity.

Based on the above disclosure, it will be understood that the exact design of the curved section(s) of the endoscope guide is/are not critical as long as an endoscope located in the lumen of the endoscope guide can be directed accurately to an intended position of a body cavity by operating the endoscope guide in such a way that the exit port of the endoscope guide defines the direction in which the endoscope is to be inserted into the body cavity.

Preferably, the functional relationship between the proximal end of the endoscope guide and the distal end of the endoscope guide allows a medical practitioner to easily and/or intuitively recognise where the endoscope, when passed through the at least one exit port of the guide, is located within the body cavity.

In an embodiment, the functional relationship determines the position of the distal end of the endoscope guide within the body cavity and defines the direction in which the endoscope exits the endoscope exit port, the direction being along the distal axis.

Therefore, the direction of movement and positioning of the endoscope within the body cavity can be accurately achieved. This allows for a greater range of movement of the endoscope distal end within the body cavity than when using conventional ports for introducing endoscopes into a body cavity. For example, the distal end of the endoscope when using the endoscope guide may be positioned to face any angle within the cavity by the medical practitioner moving the proximal end of the endoscope guide into a suitable position. The field of view of the endoscope is increased even further when an endoscope with a bendable section, as detailed above, is used. With such systems, medical practitioners may view and/or access a larger proportion of the body cavity in question than when using traditional systems.

In an embodiment, the mid-section of the endoscope guide is an essentially straight section. In other embodiments, the mid-section may adopt the form of a curve.

The mid-section of the endoscope guide comprises the endoscope entry port. Having the entry port located in the mid-section of the endoscope guide allows the medical practitioner more freedom in manoeuvring the proximal end of the endoscope guide relatively independently of the proximal end of the endoscope.

For example, whilst in use it is desirable for the direction of the distal axis of the endoscope guide, and so the direction of the distal end of the endoscope, to be altered so as to view, and/or perform a function on, a certain part of the body cavity being examined. As detailed above, the direction of the distal axis of the endoscope guide is functionally related to the movement of the proximal end of the endoscope guide. Having the endoscope entering the endoscope guide at the mid-section of the guide allows the proximal end of the guide handled to be altered without altering the position of the proximal end of the endoscope. The proximal end of the endoscope may be held in a relatively fixed position during the procedure and the endoscope guide may be handled freely without hindrance from the endoscope.

In further detail, the proximal end of the endoscope may comprise a number of additional features, such as a control lever to control the bending of the distal end of the endoscope. When using the system of the present invention, the medical practitioner may hold and control the endoscope with their non-dominant hand and position the endoscope within a body cavity by manipulating the orientation of the distal end of the endoscope guide using their dominant hand by changing the orientation of the proximal end of the endoscope guide. Through the functional relationship between the proximal section and distal section of the endoscope guide, the medical practitioner may easily determine the position of the distal section through the position of the proximal section.

It is desirable for the distal end of the endoscope guide to be easily repositioned within the body cavity. However, it is necessary for the proximal end of the endoscope to not hinder the manipulation of the endoscope guide. The entry port of the endoscope guide being located in the mid-section of the guide allows for the proximal end of the guide to be manipulated in order to position the endoscope, without any interference from the proximal end of the endoscope as the proximal end of the endoscope may be held apart and away from the proximal end of the endoscope guide.

In another embodiment, the endoscope guide may comprise an expandable section extending from the endoscope entry port located in the mid-section, which can change in length from an extended first configuration to a retracted second configuration. For example, the expandable section may be a telescopic section. Alternatively, the expandable section may be a collapsible rod extending from the endoscope entry port, wherein the expandable section comprises a series of eye guide rings through which the endoscope is passed before entering the entry port.

The expandable section ideally comprises a lumen capable of receiving an endoscope. Preferably, the expandable section extends along substantially the same axis as the mid-axis of the endoscope guide.

In this embodiment, before entering the mid-section entry port of the endoscope guide, a proportion of the proximal end of the endoscope is located in the expandable section. Upon advancing the proximal end of the endoscope towards the mid-section entry port of the endoscope guide, the expandable section gradually collapses from an extended length to a retracted length. The expandable section acts as a support to the proximal end of the endoscope. Therefore, as the proximal end of the endoscope is advanced into the guide it is retained in a substantially straight configuration before entering the mid-section entry port. Thus, the expandable section prevents the proximal end of the scope from bending or kinking, which allows for greater control over the overall positioning of the endoscope as the medical practitioner does not have to focus on ensuring that the proximal end of the endoscope does not bend. Furthermore, by preventing the endoscope from excessive bending, any components inside the endoscope, such as fibre optics, are protected from damage.

In an alternative embodiment, the entry port of the endoscope guide is an opening which is substantially flush with the outer wall of the guiding device so as to form an entry port directly through the outer wall of the endoscope guide into the lumen. In other words, some embodiments do not have such an expandable section projecting from the entry port.

The endoscope guide may comprise at least one bend located between the mid-section and the proximal section. In certain embodiments, the proximal section of the endoscope guide comprises a handle, which is typically an essentially straight handle section. The axial orientation of the essentially straight handle section of the endoscope guide defines the orientation in which the endoscope located in the lumen of the endoscope guide exits the exit port of the endoscope guide in the body cavity. According to this embodiment, the endoscope guide comprises at least two curved sections, i.e. proximal bend and distal bend, wherein the two curved sections are operably linked by a connecting section, i.e. the mid-section, which can be an essentially straight connecting section, or itself adopt the form of e.g. a curve.

The curved sections of the proximal and distal bend may essentially be circular arcs. In another embodiment, these proximal and distal bends may form a proximal and a distal angle respectively, each independently measuring more than 0 degrees, but less than 180 degrees.

In an embodiment, the proximal angle and the distal angle are selected from a group comprising acute angles, obtuse angles, right angles, and a combination thereof. In another embodiment, the proximal angle and the distal angle are selected from a group comprising a pair of supplementary angles, a pair of complementary angles, and a pair of right angles.

By observing the proximal axis direction, defined by the straight handle section in this embodiment, a medical practitioner will be able to determine the direction, i.e. distal axis direction, of the endoscope as it exits the exit port of the endoscope guide in the body cavity, as this direction is the same as the axial direction, i.e. proximal axis direction, defined by the straight handle section.

Therefore, in this embodiment, the direction of exit of the endoscope is essentially the same as the direction of the proximal axis of the proximal section.

In some embodiments, the endoscope guide is an S-shaped tube wherein the distal section, mid-section and proximal section form an S-shape. The proximal section of the endoscope guide integrates a handle which points in the same direction, i.e. defines a proximal axial direction thereof, as the axial direction in which the endoscope exits the extreme end of the distal section of the tube. In other words, the directions of the proximal axis and the distal axis are preferably the same, i.e. parallel, although the proximal end and distal end extend from the connecting mid-section in an essentially opposite direction.

In one embodiment, the angle between i) the axial direction of the endoscope when the endoscope enters the entry port of the endoscope guide, that is mid axis, and ii) the axial direction of the endoscope (located in, e.g., a body cavity) when the endoscope exits the endoscope guide from the exit port, that is distal axis thereof is preferably in the range of from 90 degrees to preferably less than 180 degrees, such as in the range of from 90 degrees to preferably less than 150 degrees, for example in the range of from 90 degrees to preferably less than 140 degrees, such as in the range of from 90 degrees to preferably less than 130 degrees, for example in the range of from 90 degrees to preferably less than 120 degrees, such as in the range of from 100 degrees to preferably less than 150 degrees, for example in the range of from 100 degrees to preferably less than 140 degrees, such as in the range of from 100 degrees to preferably less than 130 degrees, for example in the range of from 100 degrees to preferably less than 120 degrees, such as in the range of from 110 degrees to preferably less than 150 degrees, for example in the range of from 110 degrees to preferably less than 140 degrees, such as in the range of from 110 degrees to preferably less than 130 degrees, for example in the range of from 110 degrees to preferably less than 120 degrees.

In an embodiment the endoscope guide may be provided with an anchoring device which helps to place the system in the correct location of a patient's body, for example by aiding to fix the depth to which the guide is inserted into a patient's body, e.g., in the wall of a patient's abdominal cavity.

In use, the guide may be inserted into a patient's body by passing through a layer of skin, fat and muscle. The thickness of these layers, particularly the layer of fat, can vary greatly from patient to patient, so it would be useful for the user to know that the guide has been inserted to the correct depth within the patient's body to correctly and safely access and visualise the interior of the patient (such as their abdominal cavity).

The anchoring device may comprise a pump optionally connected by a tube to an inflatable cuff located on the exterior of the guide at or near the distal curve. In use, the user is able to inflate the cuff to the desired size using the pump, involving the flow of fluid (liquid or gas) through the tube to the cuff. Ideally, the cuff is located at the muscle layer, and is inflated to the desired size to fix the depth of the guide ready for use. After use, the cuff can be deflated, allowing the guide to be removed from the patient. Optionally, the proximal section of the cuff may be positioned outside of the skin of the patient in use and the distal end may be positioned beneath the skin of the patient in use. As well as being an anchoring device, the inflatable cuff may also act to prevent inflation gas in the body cavity from escaping in use.

It is envisaged that the system of the invention can be used within any body cavity. Preferably, the body cavity is a thoracic cavity, an abdominal cavity or a pelvic cavity of an animal or human body.

The cross-section of the lumen of the endoscope guide is preferably at least essentially circular so as to fit the insertion of the endoscope also having a circular cross-section. However, other geometrical cross-sections can also be envisioned.

Various polymer materials approved for surgical procedures can be used for the manufacture of the endoscope guide, including mouldable polymers of medical grade, such as polypropylene. When the guiding device is intended for multiple use the polymer composition must be sterilisable. The guiding device can also be manufactured from optionally coated titanium.

Ideally, the endoscope guide is rigid so that it can direct the advancement of the endoscope through its lumen without deforming. Preferably, the endoscope guide has a Shore A durometer hardness greater than about 40, such as from about 40 to about 100, for example from about 40 to about 90, preferably from about 50 to about 80 when tested using the ASTM D2240 method.

The endoscope guide may have a tensile strength at break of from about 2 to about 20 MPa, such as from about 5 to about 15 MPa, for example from about 5 to about 10 MPa, ideally from about 7 to about 10 MPa when tested using the ASTM D412 method.

Optionally, the endoscope guide has an elongation at break of from about 200 to about 1000%, such as from about 400 to about 1000%, for example from about 500 to about 900%, ideally from about 600 to about 900% when tested using the ASTM D412 method.

The endoscope guide preferably has a modulus at 200% elongation of from about 1 to about 10 MPa, such as from about 1 to about 5 MPa, for example from about 2 to about 5 MPa, ideally from about 2 to about 4 MPa when tested using the ASTM D412 method.

Advantageously the endoscope guide has a tear strength of from about 10 to about 100 kN/M, such as from about 20 to about 80 kN/M, for example from about 40 to 60 kN/M, ideally from about 40 to about 50 kN/M when tested using the ASTM D624 method.

In the above embodiments, the endoscopy system is described as having two main separate components, being an endoscope and an endoscope guide. However, it is fully envisaged that these two components may be integrated together into a single device, comprising any of the further embodiments detailed throughout this specification. So, in some embodiments the endoscope and guide are separate components, whereas in other embodiments the endoscope and guide are unitary.

Figure 2:
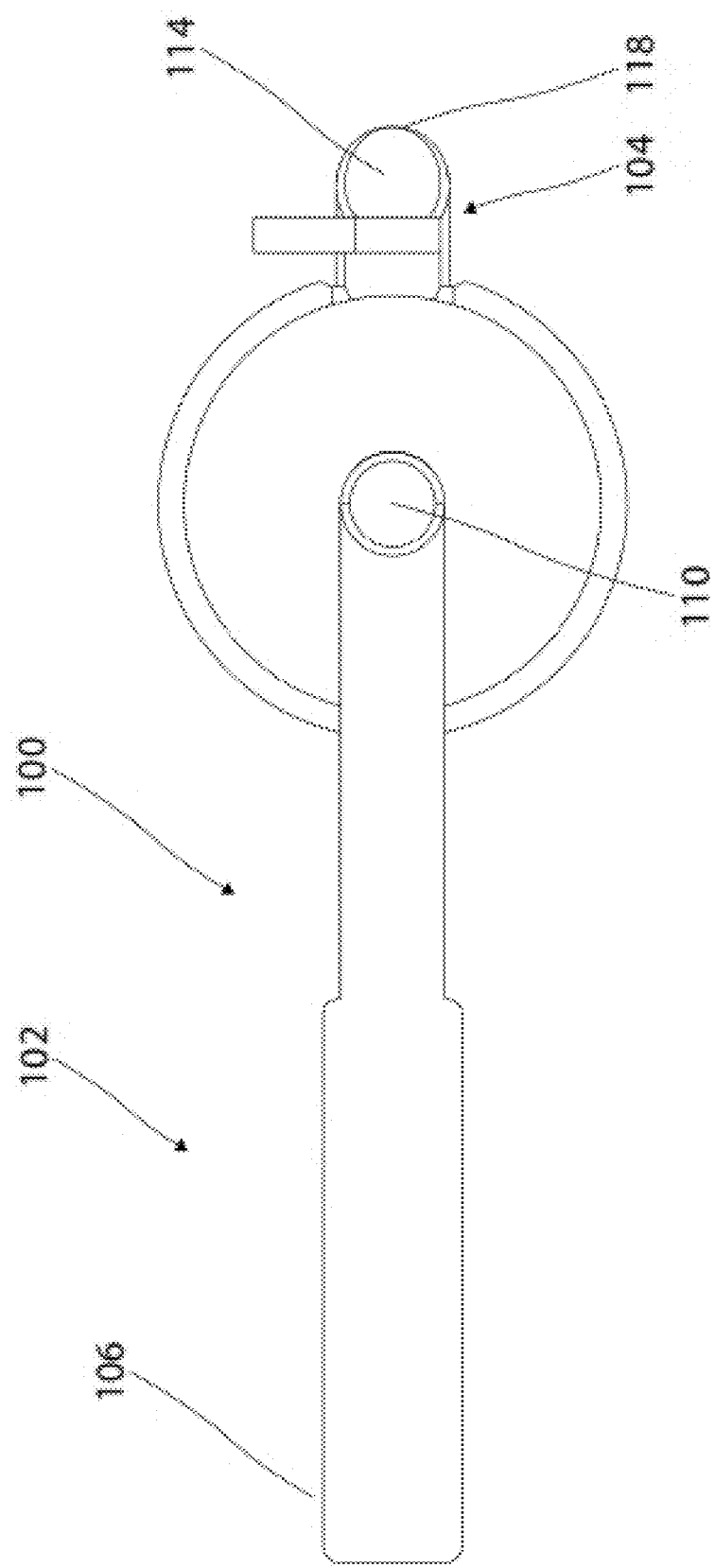
FIG. 2 is a plan view of the embodiment shown in FIG. 1.

FIGS. 1 and 2 show an embodiment of the endoscope guide (100) of the invention having a proximal portion (102) and a distal portion (104). The endoscope guide (100) is constructed from polypropylene, although other biocompatible materials, preferably polymeric materials, could be used. The proximal portion (102) contains a handle portion (106). The handle portion leads to a central substantially straight and concave mid-portion (108) of the endoscope guide, which itself leads to an opening (110) towards the distal end of the endoscope guide. The opening (110) defines an entry port for the insertion of the endoscope of the system. The outer wall of the endoscope guide forms a curved annular portion (112) leading from the entry port (110) to the distal end of the endoscope guide, forming a lumen for guiding the endoscope through the guide. The annular portion leads to an opening (114) defining the exit port for the endoscope.

The handle portion (106) of the endoscope guide defines a proximal axis having a proximal direction. The distal portion (104) and the mid-portion (108), defined by their respective distal axis and mid-axis, form a distal angle defining a distal bend. Similarly, the proximal portion (102) and the mid-portion (108), defined by their respective proximal axis and mid-axis, form a proximal angle defining a proximal bend.

The proximal angle and the distal angle share a relation defining a functional relationship between the movement of the distal end and the proximal end. The endoscope enters the lumen of the endoscope guide through the entry port (110) and is diverted through the lumen, defined between the entry port (110) and the exit port (114), of the endoscope guide by a medical practitioner and exits the endoscope guide at the distal end thereof in a direction of the distal axis. In this embodiment, the direction of exit of the endoscope is at least essentially similar to the proximal axis direction. However, in other embodiments, the direction of exit of the chest tube is not essentially parallel to that of the direction of the proximal axis.

By observing the relationship between the directions of the proximal axis and distal axis of the endoscope guide, as defined by the proximal angle and distal angle, relative movement of the distal end with respect to the proximal end may be determined and thus, the medical practitioner will be able to ascertain the direction in which the endoscope is inserted into the body cavity of the individual.

The outer wall of the guide defines a projecting rim, or collar, (116) distal of the entry port (110) to provide the user with a defined stopping point to aid the correct insertion of the endoscope guide (100) into a patient's body. The guide (100) is inserted into the patient's body until the rim (116) comes near to or contacts the patient's skin. The distal end (104) of the endoscope guide (100) is also provided with a projecting tip (118). In this embodiment shown, the tip is in the form of a lip (118) projecting beyond the exit port (114). The lip (118) aids the insertion of the device into a patient's body.

Figure 3:
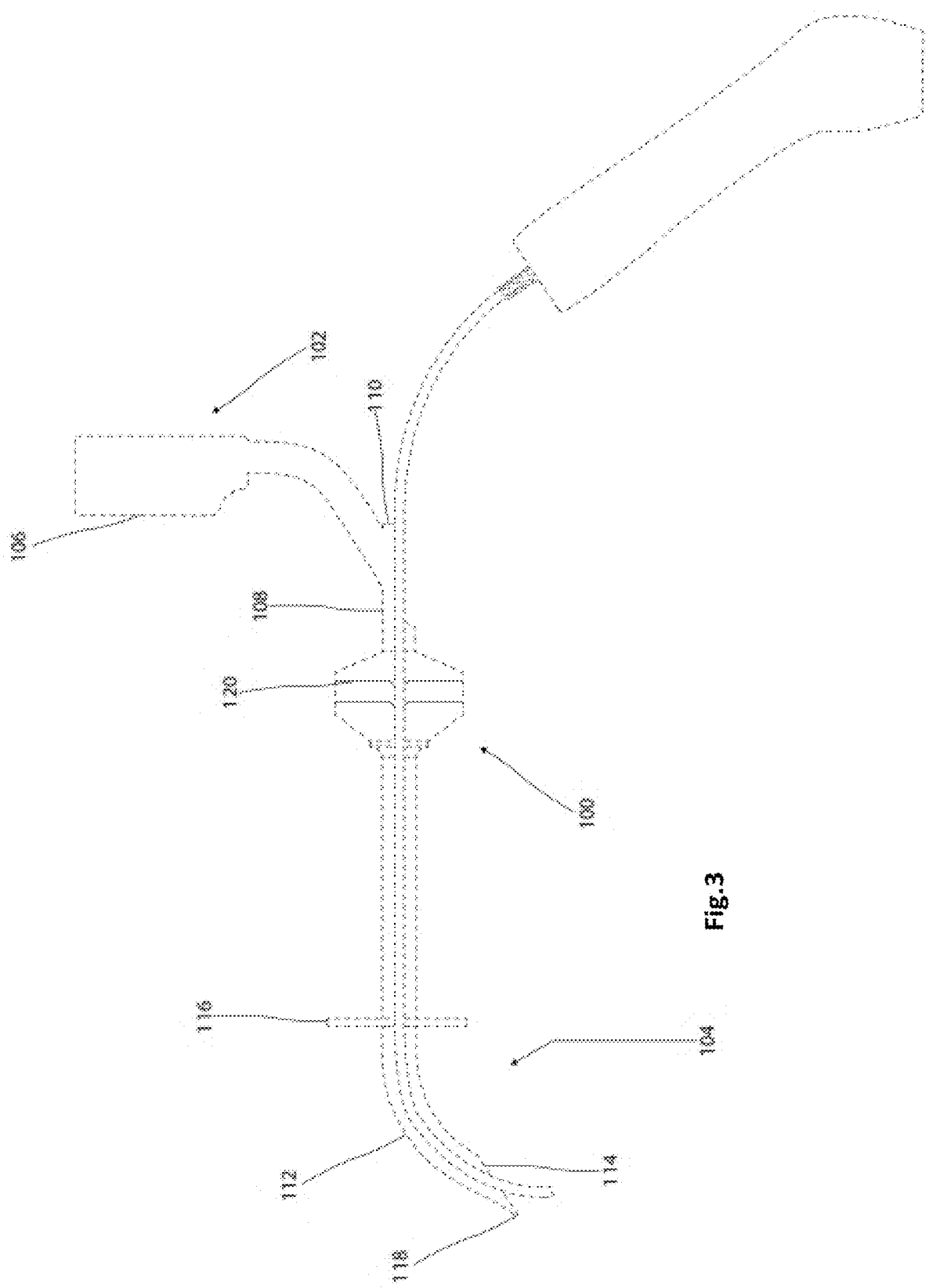
FIG. 3 is a cross-sectional view of the endoscope guide of FIG. 1 comprising a pinch valve.
Figure 4:
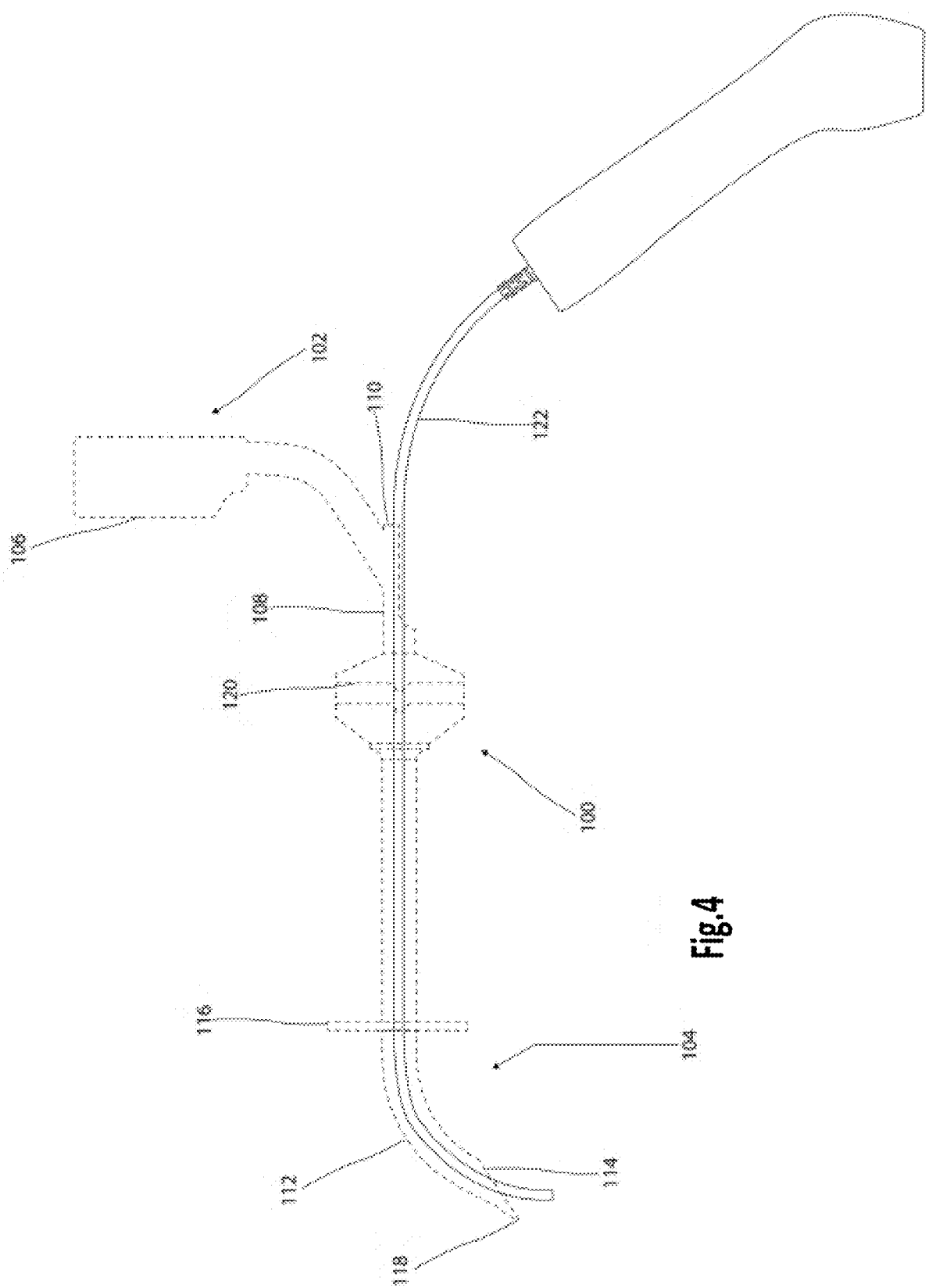
FIG. 4 relates to FIG. 3 wherein an endoscope is placed within the lumen of the endoscope guide and through the pinch valve.

FIGS. 3 and 4 detail a cross-section of the guide of FIGS. 1 and 2. In this embodiment of the endoscope guide a pinch valve (120) is located between the endoscope entry port and the endoscope exit port. In FIG. 3 the valve is tapered to a flattened end with the opening effectively sealed so as to prevent back flow of pressurised gas in the body cavity escaping through the lumen of the endoscope guide.

In FIG. 4 an endoscope (122) is located within the lumen of the endoscope guide and it can be seen that the flattened end of the valve (120) opens up to allow the endoscope to pass through the lumen and creates a seal around the circumference of the endoscope.

Figure 5:
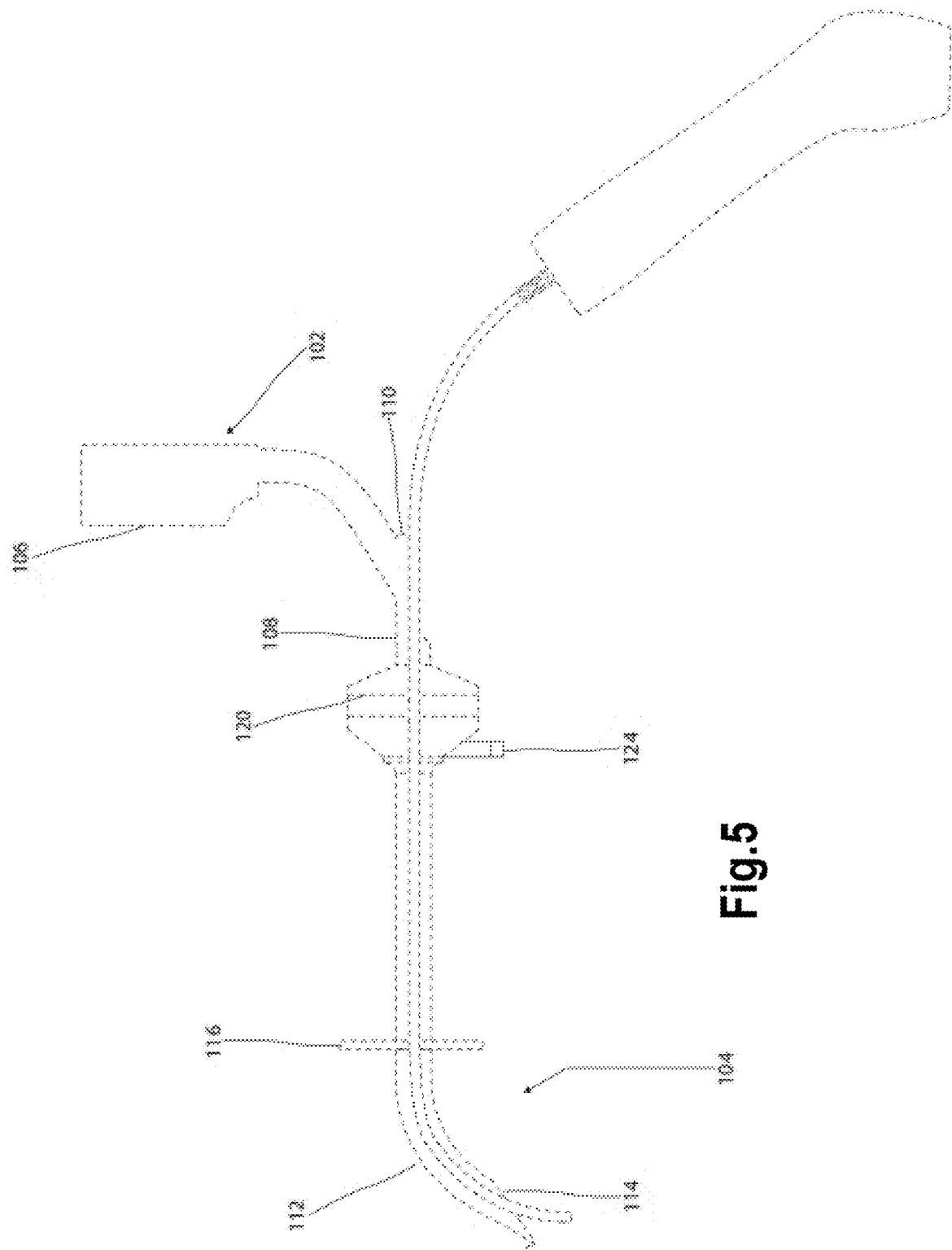
FIG. 5 relates to FIG. 3, wherein the endoscope guide further comprises a gas insufflation connector.
Figure 6:
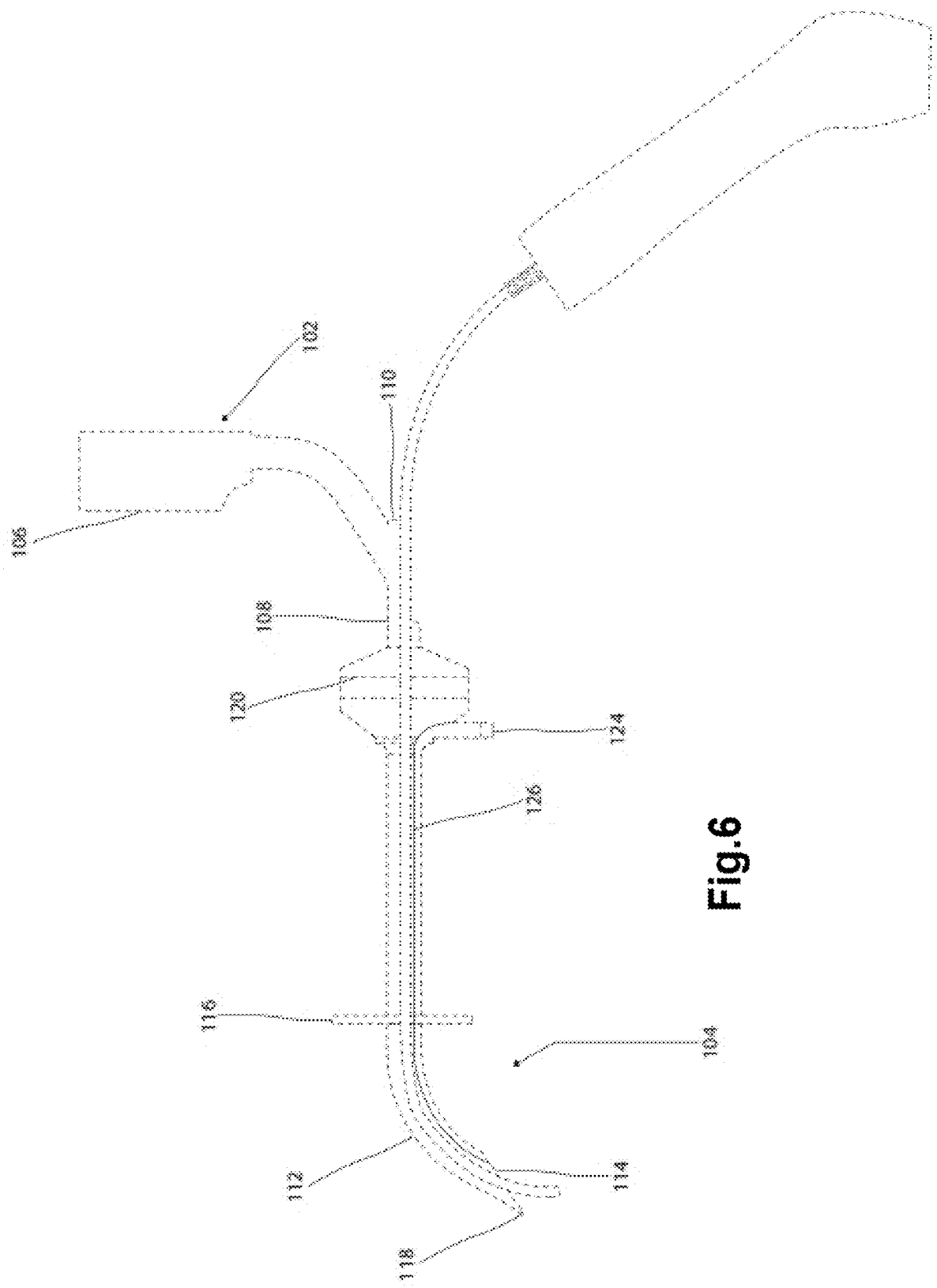
FIG. 6 relates to FIG. 5, wherein in the endoscope guide shown, there is included a second lumen extending from the gas insufflation connector to the exit port of the guide.

FIGS. 5 and 6 correspond to FIGS. 3 and 4. However, in these embodiments, the endoscope guide device comprises a gas insufflation connector (124). Preferably the gas insufflation connector (124) is a luer fitting, such as a luer lock or luer slip connector. The gas insufflation connector (124) may be connected to any suitable gas source. In both of these embodiments, the gas insufflation connector (124) is located distally of the valve, which allows for gas to be introduced through the lumen and into the body cavity of an individual, wherein the valve prevents back flow of the gas out of the body cavity through the lumen of the endoscope guide.

The gas insufflation connector (124) may connect directly to the lumen through which the endoscope is directed through, as shown in FIG. 5. Alternatively, as shown in FIG. 6, the gas insufflation connector (124) may connect to a second lumen (126) located within the first lumen, wherein the second lumen extends from the gas insufflation connector (124) to the exit port of the endoscope guide. Although the embodiments shown in FIGS. 5 and 6 both detail the combination of a valve with a gas insufflation connector (124), it is envisaged that either of these features may be incorporated into the device separately. For example, the endoscope guide may comprise a gas insufflation connector (124), but not a one-way valve. Alternatively, the endoscope guide may comprise a one-way valve, but not a gas insufflation connector.

Figure 7:
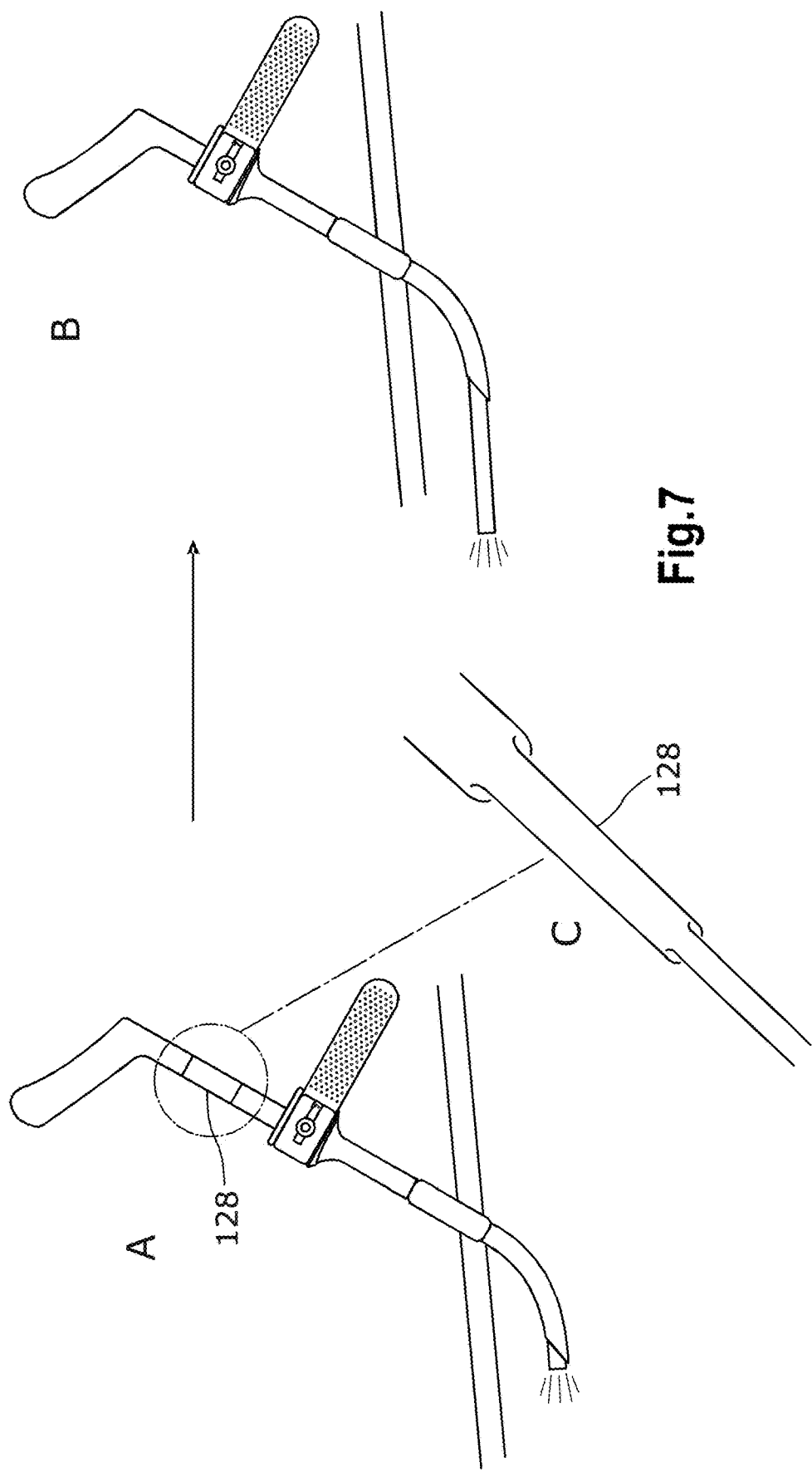
FIG. 7 details an embodiment of the system of the invention wherein the endoscope guide comprises an expandable section.

FIG. 7 details a further embodiment of the invention. Specifically, the system in this figure corresponds to any of the figures detailed above, with the addition that the endoscope guide comprises an expandable section (128), in this case a telescopic section. FIG. 7A shows the expandable section in a first extended configuration, with a close up image shown in FIG. 7C.

The expandable section extends along substantially the same axis as the mid-axis of the endoscope guide. Upon advancing the proximal end of the endoscope towards the mid-section entry port of the endoscope guide, the expandable section collapses to a retracted configuration as shown in FIG. 7B. The endoscope is advantageously guided through the endoscope guide and out of the exit port during the advancement shown in FIG. 7.

Figure 8:
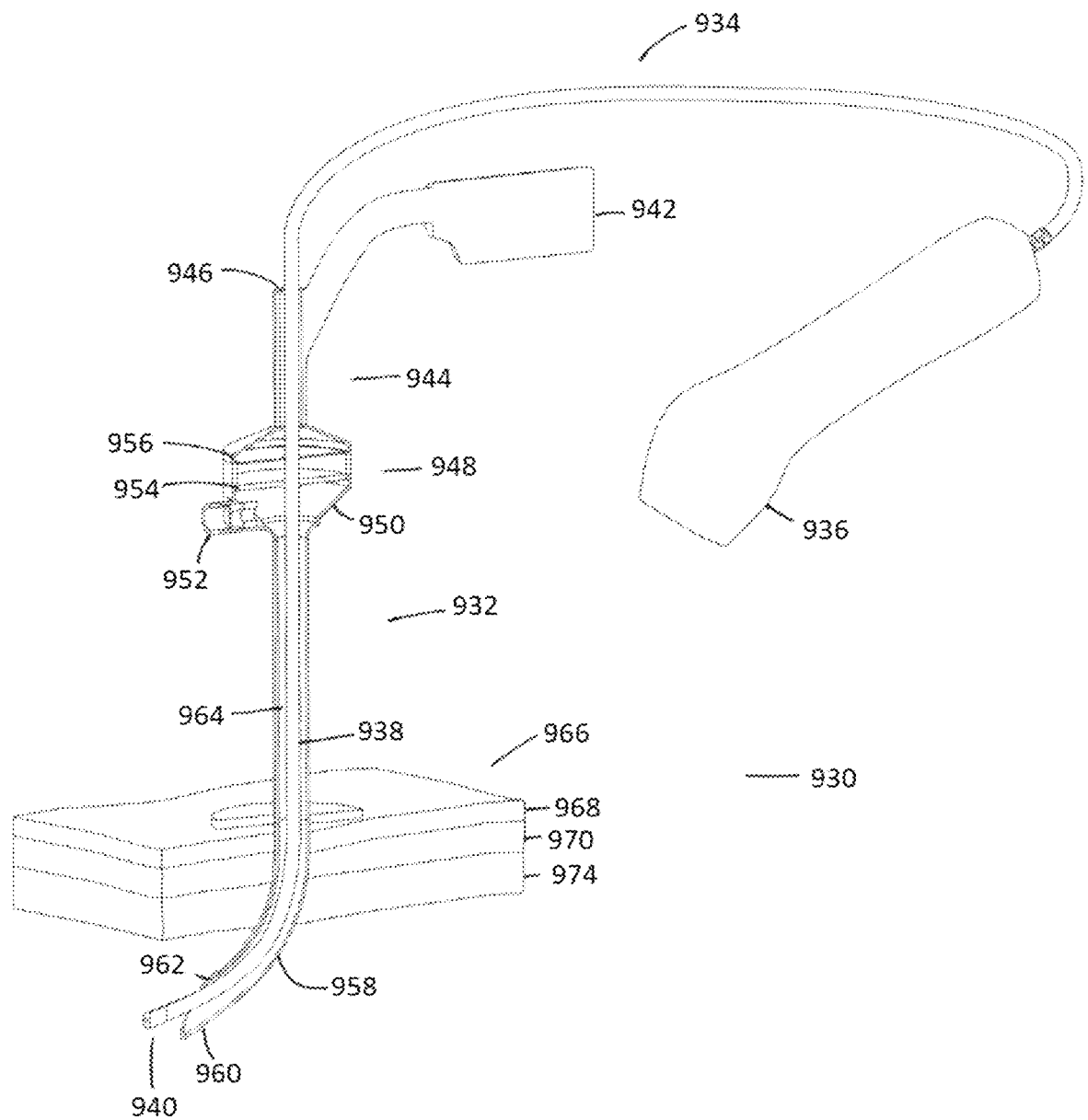
FIG. 8 is a partial cross-sectional view of another embodiment of an endoscope guide in use with a patient.

FIG. 8 shows an endoscopy system of the invention (930) in use with a patient (966). The system (930) comprises a guide (932) into which is positioned an endoscope (934).

The endoscope has a handle portion (936) at the proximal end, which is held by the user and has controls to control aspects of the endoscope's function. The guide has a handle portion (942) at the proximal end which is held and manipulated by the used to control the position of the guide (932) and in particular the position and direction of the distal end (960) of the guide (932).

Turning back to the endoscope (934), the proximal handle portion (936) leads to the slender portion of the endoscope (938), which passes into an endoscope entry port (946) located in the mid-section (944) of the guide (932). The slender portion (938) of the endoscope passes through the lumen (964) of the guide towards the endoscope exit port (962) located at the distal end (960) of the guide (932).

The guide (932) extends from the mid-section (944) in a substantially straight manner, to a curved section (958) near the distal end (960) of the guide (932). Before the curved section (958) there is located a gas insufflation portion (948) which allows for gas to be introduced through the guide (932) and into the patient (966) in order to facilitate use of the endoscope (934) within the patient's body.

The gas insufflation portion (948) comprises a chamber (950) formed by a section of the guide with an enlarged diameter, through which the endoscope (934) passes. A gas inlet (952) leads into the chamber (950) and allows for the introduction of gas into the lumen (964) of the guide, and thus into the patient's body. To limit or prevent gas escaping from the guide, a first valve (954) and a second valve (956) are located within the chamber (950) to form a close fit around the endoscope (934).

The endoscope (934) passes through the gas insufflation portion (948), is guided through the curved section (958) of the guide and out of the endoscope exit port (962) at the distal end (960) of the guide (932). The distal end (940) of the endoscope (934) is provided with a light and a camera.

As shown, the guide (932) is inserted into the patient's body by passing through a layer of skin (968), fat (970) and muscle (974).

Figure 9:
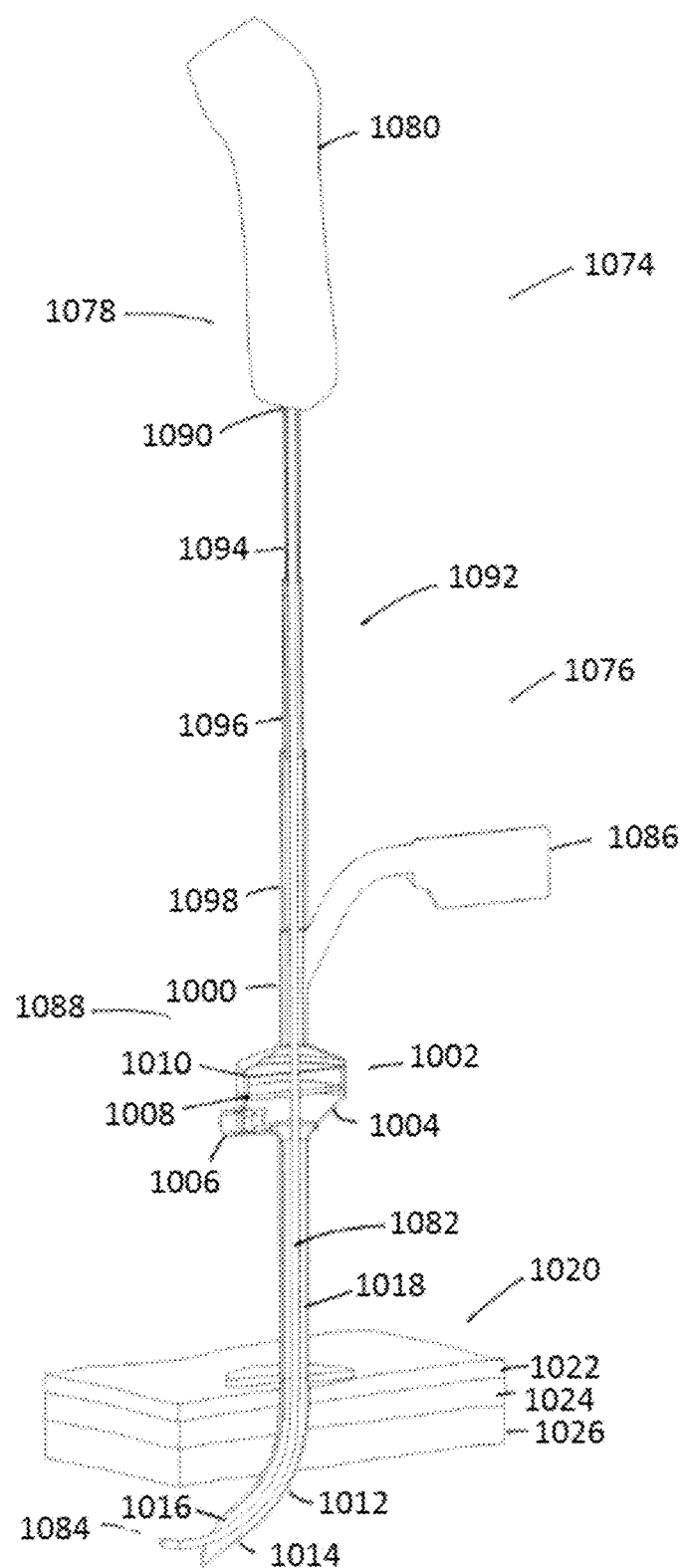
FIG. 9 is a partial cross-sectional view of another embodiment of an endoscope guide with a telescopic portion in use with a patient.

FIG. 9 shows another endoscopy system of the invention (1074) in use with a patient (1020). The system (1074) comprises a guide (1076) into which is positioned an endoscope (1078). The endoscope (1078) has a handle portion (1080) at the proximal end, which is held by the user and has controls to control aspects of the endoscope's function. The guide (1076) has a handle portion (1086) at the proximal end which is held and manipulated by the used to control the position of the guide (1076) and in particular the position and direction of the distal end (1014) of the guide (1076).

A difference between the system (1074) shown in FIG. 9 and the system (930) shown in FIG. 8 is in the structure of the mid-section (1088) of the guide (1076) where the endoscope (1078) enters the guide (1076). As mentioned above, a user may be holding the handle (1080) of the endoscope (1078) in one hand and the handle (1086) of the guide (1076) in their other hand. The user will push the endoscope (1078) into the guide (1076) to allow the distal tip (1084) of the endoscope to be inserted through the guide (1076), to the endoscope exit port (1016) inside the body of the patient (1020). However, the slender endoscope can be quite flexible, and so there can be problems when the user attempts to push the endoscope (1078) into the guide (1076). This can be, for example, the endoscope (1078) bending or kinking before it passes into and through the guide (1076). The system (1074) addresses this potential issue by provided an expandable section (1092) in the region of the guide (1076) where the endoscope (1078) is inserted. As shown, the endoscope (1078) enters an endoscope entry port (1090)

located at the expandable section (1092) of the guide (1076). In the embodiment shown, the expandable section (1092) comprises 3 telescope sections (1094, 1096 and 1098), which extend from the mid-section (1088) of the guide (1076). The slender section of the endoscope (1082) is thus supported and guided by the expandable section (1092) of the guide (1076) as the user pushes the endoscope (1078) into the guide (1076), preventing unwanted bending or kinking. The telescopic sections (1094, 1096, 1098), collapse into each other as concentric cylinders as the endoscope (1078) is inserted into the guide (1076), and into a portion (1000) of the mid-section (1088) of the guide.

The guide (1076) extends from the mid-section (1088) in a substantially straight manner, to a curved section (1012) near the distal end (1014) of the guide (1076). Before the curved section (1012) there is located a gas insufflation portion (1002) which allows for gas to be introduced through the guide (1076) and into the patient (1020) in order to facilitate use of the endoscope (1078) within the patient's body.

The gas insufflation portion (1002) comprises a chamber (1004) formed by a section of the guide with an enlarged diameter, through which the endoscope (1078) passes. A gas inlet (1006) leads into the chamber (1004) and allows for the introduction of gas into the lumen (1018) of the guide, and thus into the patient's body. To limit or prevent gas escaping from the guide, a first valve (1008) and a second valve (1010) are located within the chamber (1004) to form a close fit around the endoscope (1078).

The endoscope (1078) passes through the gas insufflation portion (1002), is guided through the curved section (1012) of the guide and out of the endoscope exit port (1016) at the distal end (1014) of the guide (1076). The distal end (1084) of the endoscope (1078) is provided with a light and a camera.

As shown, the guide (1076) is inserted into the patient's body by passing through a layer of skin (1022), fat (1024) and muscle (1026).

Figure 10:
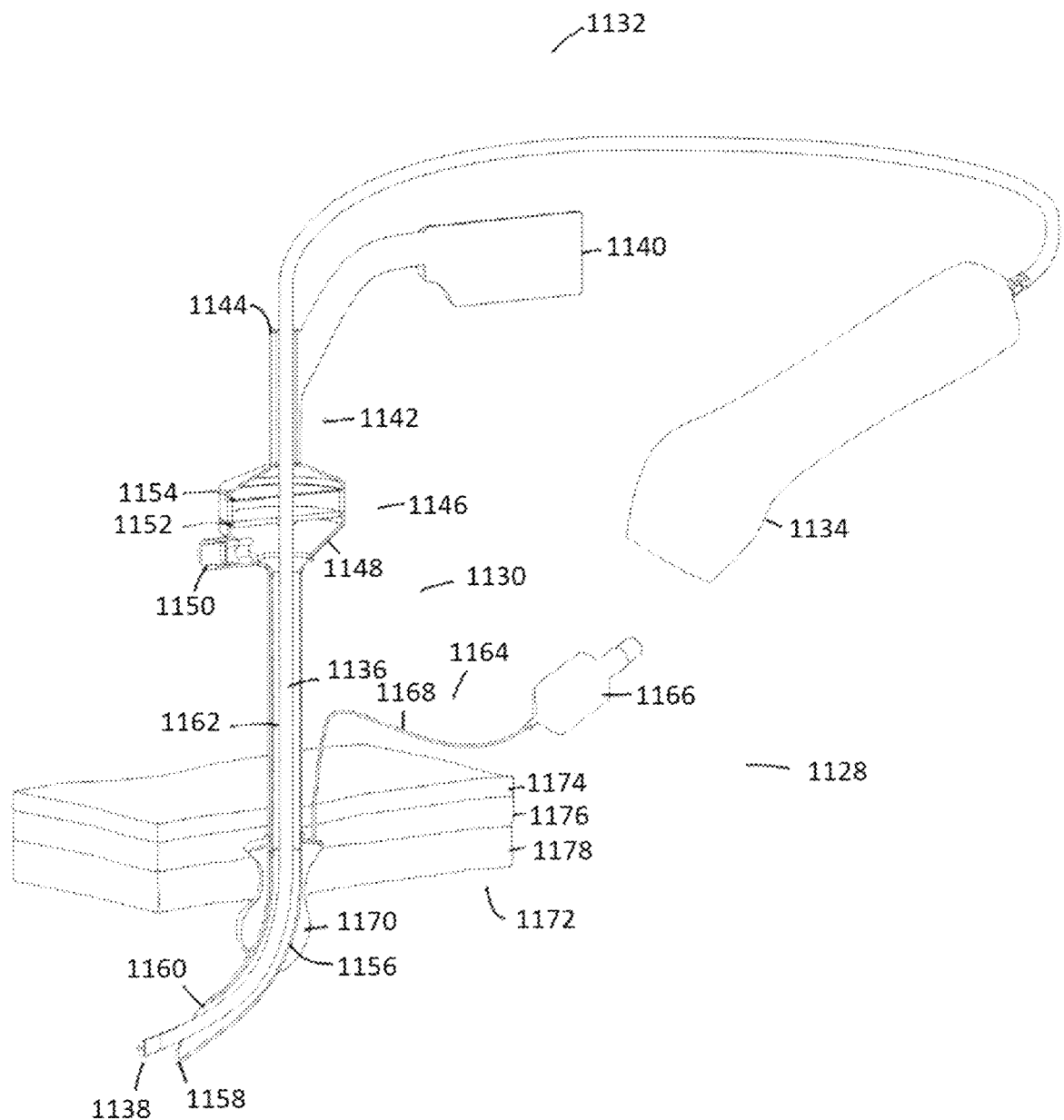
FIG. 10 is a partial cross-sectional view of another embodiment of an endoscope guide with an anchoring system in use with a patient.

FIG. 10 shows another endoscopy system of the invention (1128) in use with a patient (1172). The system (1128) comprises a guide (1130) into which is positioned an endoscope (1132). The endoscope (1132) has a handle portion (1134) at the proximal end, which is held by the user and has controls to control aspects of the endoscope's function. The guide has a handle portion (1140) at the proximal end which is held and manipulated by the used to control the position of the guide (1130) and in particular the position and direction of the distal end (1158) of the guide (1130).

Turning back to the endoscope (1132), the proximal handle portion (1134) leads to the slender portion of the endoscope (1136), which passes into an endoscope entry port (1144) located in the mid-section (1142) of the guide (1130). The slender portion (1136) of the endoscope passes through the lumen (1162) of the guide towards the endoscope exit port (1160) located at the distal end (1158) of the guide (1130).

The guide (1130) extends from the mid-section (1142) in a substantially straight manner, to a curved section (1156) near the distal end (1158) of the guide (1130). Before the curved section (1156) there is located a gas insufflation portion (1146) which allows for gas to be introduced through the guide (1130) and into the patient (1172) in order to facilitate use of the endoscope (1132) within the patient's body.

The gas insufflation portion (1146) comprises a chamber (1148) formed by a section of the guide with an enlarged diameter, through which the endoscope (1132) passes. A gas inlet (1150) leads into the chamber (1148) and allows for the introduction of gas into the lumen (1163) of the guide, and thus into the patient's body. To limit or prevent gas escaping from the guide, a first valve (1152) and a second valve (1154) are located within the chamber (1148) to form a close fit around the endoscope (1132).

The endoscope (1132) passes through the gas insufflation portion (1146), is guided through the curved section (1156) of the guide and out of the endoscope exit port (1160) at the distal end (1158) of the guide (1130). The distal end (1138) of the endoscope (1132) is provided with a light and a camera.

This system (1128) is provided with an anchoring device (1164) which helps to place the system (1130) in the correct location of the patient's body. In particular, the anchoring device (1164) helps to fix the depth to which the guide (1130) is inserted into the patient's body, for example in the wall of the patient's abdominal cavity. Furthermore, the anchoring device also aids in preventing inflation gases in the body cavity from escaping around the outside of the device.

As shown, the guide (1130) is inserted into the patient's body by passing through a layer of skin (1174), fat (1176) and muscle (1178). The thickness of these layers, particularly the layer of fat, can vary greatly from patient to patient, so it would be useful for the user to know that the guide (1130) has been inserted to the correct depth within the patient's body to correctly and safely access and visualise the interior of the patient (such as their abdominal cavity).

The anchoring device shown comprises a pump (1166) connected by a tube (1168) to an inflatable cuff (1170) located on the exterior of the guide (1130) at or near the distal curve (1156). In use, the user can inflate the cuff (1170) to the desired size using the pump (1166), involving the flow of fluid (liquid or gas) through the tube (1168) to the cuff (1170). Ideally, the cuff (1170) is located at the muscle layer (1178), and is inflated to the desired size to fix the depth of the guide (1130) ready for use. After use, the cuff (1170) can be deflated, allowing the guide (1130) to be removed from the patient.

Figure 11:
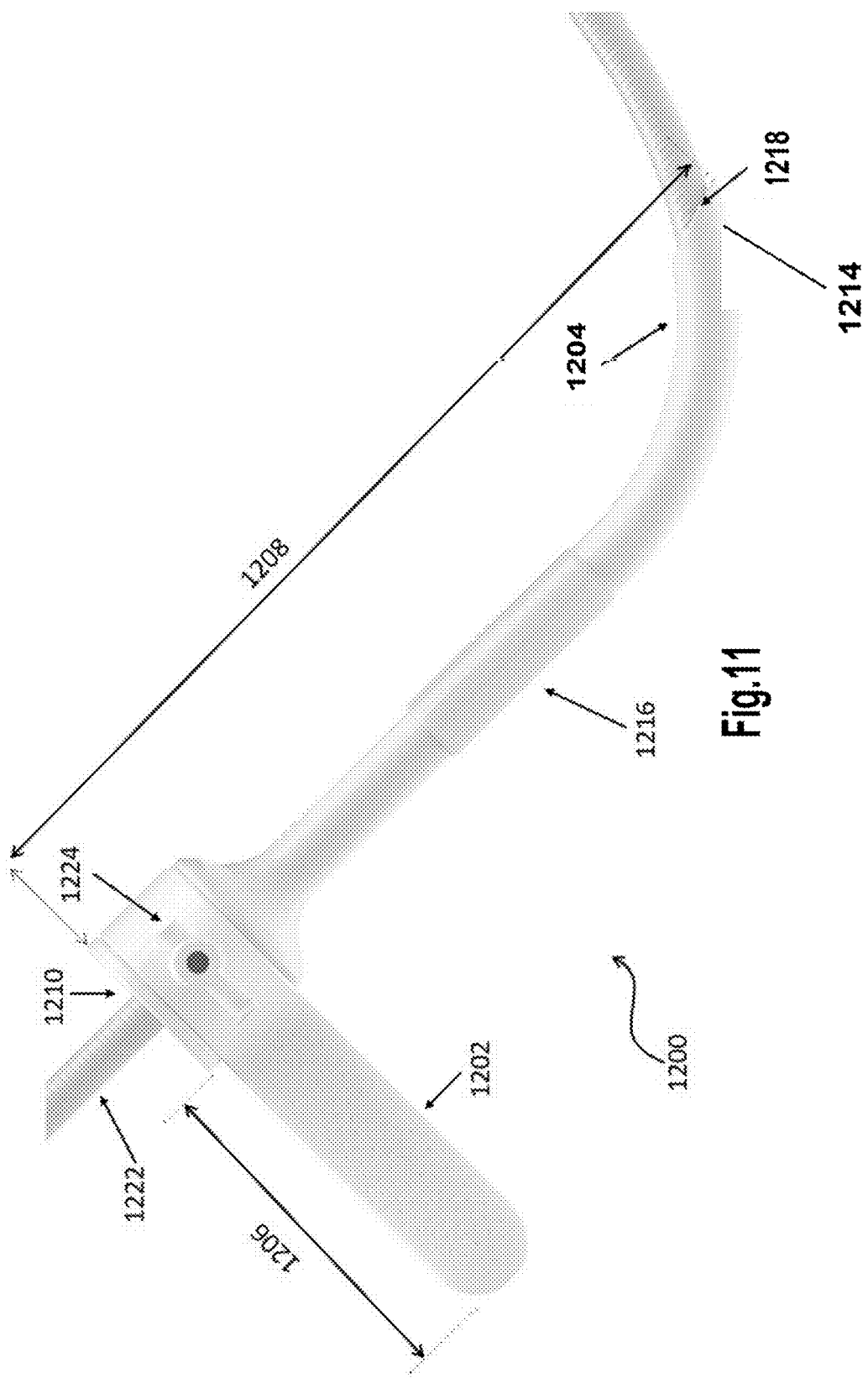
FIG. 11 illustrates another embodiment of the endoscope guide of the system.
Figure 12:
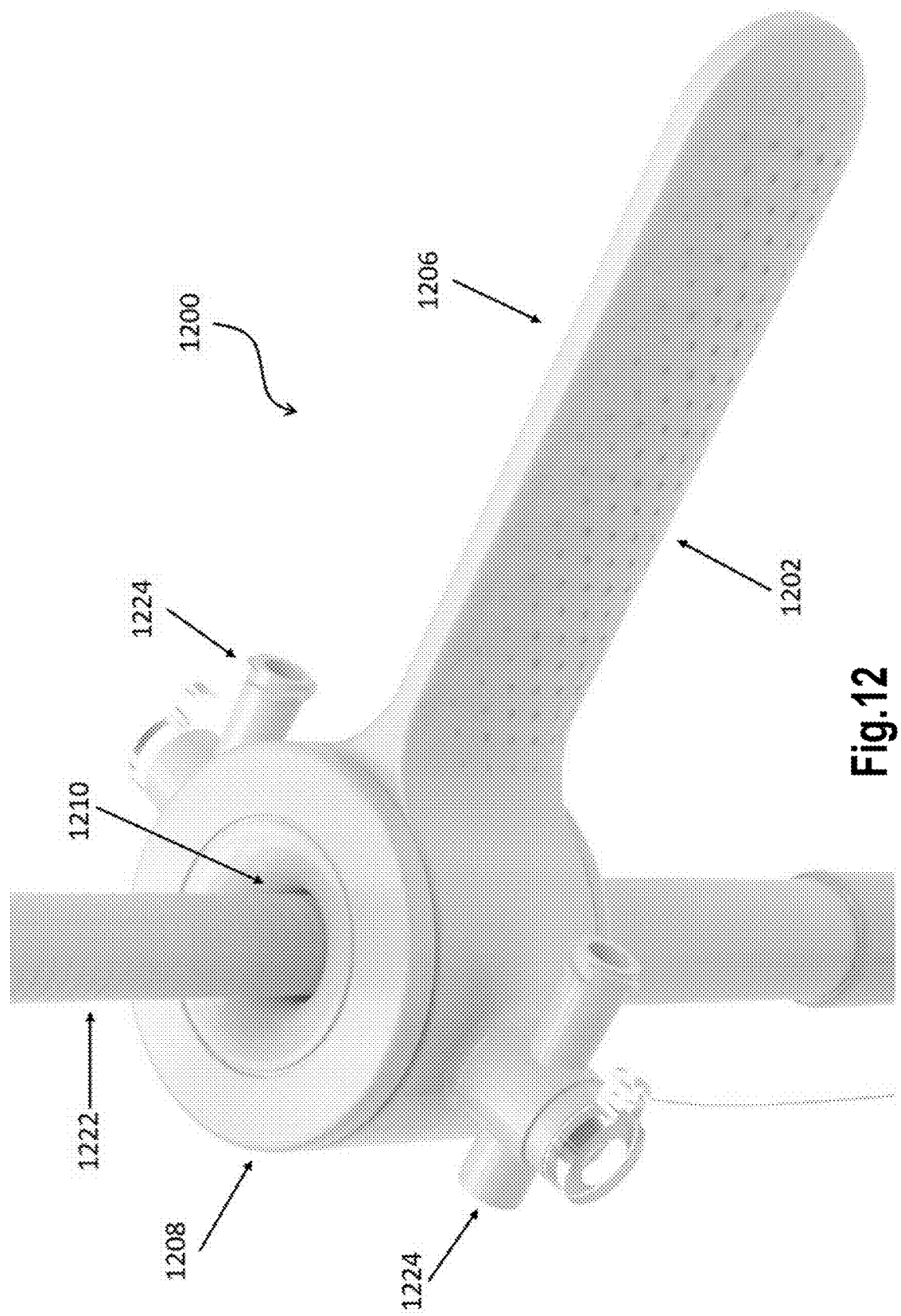
FIG. 12 is a top view of the endoscope guide system illustrated in FIG. 11.

FIGS. 11 and 12 show another embodiment of the endoscope guide (1200) of the invention. Like the guides outlined in FIGS. 1 to 10, the guide of FIGS. 11 and 12 has a proximal portion (1202) and a distal portion (1204). The endoscope guide (1200) is constructed from polypropylene, although other biocompatible materials, preferably polymeric materials, could be used. The proximal portion (1202) contains a handle portion (1206). The handle portion leads to a central substantially straight mid-portion (1208) of the endoscope guide, which itself has an opening (1210). The opening (1210) defines an entry port for the insertion of the endoscope (1222) of the system. The entry port (1210) may be better seen in FIG. 12.

The outer wall of the endoscope guide forms a curved annular portion leading from the entry port (1210) to the distal end of the endoscope guide, forming a lumen for guiding the endoscope through the guide. The annular portion leads to an opening (1214) defining the exit port for the endoscope.

The handle portion (1206) of the endoscope guide defines a proximal axis having a proximal direction. The distal portion (1204) and the mid-portion (1208), defined by their respective distal axis and mid-axis, form a distal angle defining a distal bend. Similarly, the proximal portion (1202) and the mid-portion (1208), defined by their respective proximal axis and mid-axis, form a proximal angle defining a proximal bend. In this embodiment, the proximal section comprises a handle defining the proximal axis, which extends at a substantially right angle (90°) to the mid-axis.

The proximal angle and the distal angle share a relation defining a functional relationship between the movement of the distal end and the proximal end. The endoscope enters the lumen of the endoscope guide through the entry port (1210) and is diverted through the lumen, defined between the entry port (1210) and the exit port (1214), of the endoscope guide by a medical practitioner and exits the endoscope guide at the distal end thereof in a direction of the distal axis.

By observing the relationship between the directions of the proximal axis and distal axis of the endoscope guide, as defined by the proximal angle and distal angle, relative movement of the distal end with respect to the proximal end may be determined and thus, the medical practitioner will be able to ascertain the direction in which the endoscope is inserted into the body cavity of the individual.

The outer wall of the guide defines a projecting rim, or collar, (1216) distal of the entry port (1210) to provide the user with a defined stopping point to aid the correct insertion of the endoscope guide (1200) into a patient's body. The guide (1200) is inserted into the patient's body until the rim (1216) comes near to or contacts the patient's skin. The distal end (1204) of the endoscope guide (1200) is also provided with a projecting tip (1218). In this embodiment shown, the tip is in the form of a lip (1218) projecting beyond the exit port (1214). The lip (1218) aids the insertion of the device into a patient's body.

In this embodiment, the endoscope guide device comprises two gas insufflation connectors (1224). Preferably the gas insufflation connector (1224) is a luer fitting, such as a luer lock or luer slip connector. The gas insufflation connector (1224) may be connected to any suitable gas source.

In another aspect the present invention provides a kit-of-parts comprising an endoscopy system as detailed above. The kit-of-parts is preferably a sterile, pre-packaged kit-of-parts for single use only. The contents of the kit-of-parts can be separated from an external environment by a sterile barrier seal which is broken immediately prior to using the contents of the kit-of-parts in a surgical procedure.

The kit-of-parts can be for emergency use and may optionally further comprise one or more of a scalpel, a needle and sutures, a pair of surgical scissors, a clamp, a disinfectant, anaesthetic, cover, gauze, dressings, and a suction device and/or a collection bag. The kit-of-parts may comprise multiple endoscopes of different sizes and/or one or more endoscope guides capable of being operably used in combination with said endoscopes of different sizes.

A further aspect of the invention is a method for inserting an endoscope into a body cavity of an individual comprising the steps of providing an endoscopy system as detailed above and inserting the endoscope into the body cavity of the individual using the endoscope guide.

Preferably, the body cavity is a thoracic cavity, an abdominal cavity or a pelvic cavity of an animal or human body.

We claim:

1. An endoscopy system comprising a rigid endoscope guide and an endoscope, wherein the endoscope comprises:
    a proximal section with a proximal end; and
    a distal section with a distal end;
    wherein, the rigid endoscope guide comprises:
    a proximal section with a proximal end and a handle;
    a mid-section comprising at least one endoscope entry port;
    a distal section with a distal end comprising at least one endoscope exit port;
    a lumen extending from the at least one endoscope entry port to the at least one endoscope exit port, said lumen configured to receive the endoscope; and
    at least one distal bend located between the at least one endoscope entry port and the at least one endoscope exit port;
    wherein, the rigid endoscope guide is configured to direct an insertion of the distal end of the endoscope into a body cavity when the distal end of the endoscope exits the endoscope exit port;
    at least one proximal bend located between the mid-section and the proximal section;
    the distal end of the rigid endoscope guide is also configured so as to be retained within the body cavity during a surgical procedure so as to control a positioning of the distal end of the endoscope within the body cavity,
    wherein, the rigid endoscope guide is configured with a fixed functional relationship between a rotation of the proximal end of the rigid endoscope guide and a corresponding rotation of the distal end of the rigid endoscope guide, so that an orientation of the proximal end of the rigid endoscope guide defines an axis exit direction in which the distal end of the endoscope located in the lumen exits the endoscope exit port of the rigid endoscope guide in the body cavity, when disposed therethrough, and
    wherein the rigid endoscope guide comprises a gas insufflation portion comprising a gas insufflation connector and a chamber formed by a section of the rigid endoscope guide, and wherein the chamber has an inner diameter which is larger than an inner diameter of portions of the lumen of the rigid endoscope guide that are distal of and proximal of the chamber.

2. The endoscopy system of claim 1, wherein the endoscope is a laryngoscope, esophagoscope, thoracoscope, pleuroscope, laparoscope, bronchoscope, mediastinoscope, gastroscope, or an amnioscope.

3. The endoscopy system according to claim 1, wherein the rigid endoscope guide comprises a one-way valve located in the lumen between the at least one endoscope entry port and the at least one endoscope exit port, wherein the valve is configured so as to prevent gas from passing through the lumen of the rigid endoscope guide.

4. The endoscopy system according to claim 1, wherein the mid-section is a straight section.

5. The endoscopy system according to claim 1, wherein the proximal section of the rigid endoscope guide defines a proximal axis, the distal section of the rigid endoscope guide defines a distal axis and the proximal axis and distal axis are parallel to one another so that a direction of exit of the endoscope from the at least one endoscope exit port is the same as a direction of the proximal axis of the proximal section.

6. The endoscopy system according to claim 1, wherein the body cavity is a thoracic cavity, an abdominal cavity, or a pelvic cavity of an animal or human body.

7. The endoscopy system according to claim 1, where the rigid endoscope guide comprises a collar with a diameter larger than a diameter of the rigid endoscope guide, wherein the collar is located between the at least one endoscope entry port and the distal bend.

8. The endoscopy system according to claim 1, wherein the rigid endoscope guide comprises an expandable section extending from the endoscope entry port located in the mid-section.

9. The endoscopy system according to claim 1, wherein the rigid endoscope guide is constructed from a polymeric material.

10. The endoscopy system according to claim 1, wherein the distal end of the rigid endoscope guide has a projecting tip in the form of a lip projecting beyond the endoscope exit port.

11. The endoscopy system according to claim 1, wherein the rigidity of the rigid endoscope guide provides for an advancement of the endoscope through the lumen of the rigid endoscope guide without deforming.

12. The endoscopy system according to claim 1, wherein the rigid endoscope guide has a Shore A durometer hardness of from 40 to 100.

13. The endoscopy system according to claim 1, wherein the rigid endoscope guide has a tensile strength at break of from 2 to 20 MPa.

14. The endoscopy system according to claim 1, wherein the rigid endoscope guide has a tear strength of from 10 to 100 kN/M.

15. The endoscopy system according to claim 1, wherein the mid-section defines a mid-axis and the handle extends at a right angle to the mid-axis.

16. The endoscopy system according to claim 1, wherein the gas insufflation portion comprises two gas insufflation connectors.

17. The endoscopy system according to claim 3, wherein the valve is configured to allow the endoscope to pass through the lumen and create a seal around a circumference of the endoscope.

18. The endoscopy system according to claim 1, wherein the gas insufflation connector connects to another lumen located within the lumen, and wherein the another lumen extends from the gas insufflation connector to the endoscope exit port of the rigid endoscope guide.

* * * * *